United States Patent [19]

Romain

[11] 4,001,650
[45] Jan. 4, 1977

[54] METHOD AND APPARATUS FOR ULTRASONIC TRANSDUCER PROTECTION

[75] Inventor: Jack Romain, Santa Monica, Calif.

[73] Assignee: Puritan-Bennett Corporation, Kansas City, Mo.

[22] Filed: Sept. 2, 1975

[21] Appl. No.: 609,310

[52] U.S. Cl. .............................. 317/41; 128/DIG. 2; 310/8.1

[51] Int. Cl.² ......................................... H02H 5/04

[58] Field of Search ................ 317/40 R, 41, 42; 340/228 R; 128/193, 194, DIG. 2; 310/8.1

[56] References Cited
UNITED STATES PATENTS

| | | | |
|---|---|---|---|
| 2,937,640 | 5/1960 | Bastir | 310/8.1 X |
| 3,593,712 | 7/1971 | Weaver et al. | 128/DIG. 2 |
| 3,828,773 | 8/1974 | Buch et al. | 128/DIG. 2 |

Primary Examiner—Harry Moose
Attorney, Agent, or Firm—Fulwider Patton Rieber, Lee & Utecht

[57] ABSTRACT

Apparatus and a corresponding method for the protection of an ultrasonic transducer operating immersed in a liquid, such as in an ultrasonic nebulizer. Surface motion of the liquid is detected by analysis of the voltage across the transducer terminals, and this surface motion indication is combined with a transducer temperature indication to determine whether or not the transducer should be shut off to prevent destruction or damage due to overheating or absence of surrounding water. Once turned off, the transducer cannot be re-energized without the removal and reapplication of electrical power to the apparatus. Provision is made for allowing the transducer to remain on even when no surface motion is present, provided the temperature is below a certain value, to permit adjustment of the transducer circuit while the transducer is in operation. An alarm is actuated when the transducer is turned off to call attention to the high temperature or loss of surface motion.

19 Claims, 3 Drawing Figures

METHOD AND APPARATUS FOR ULTRASONIC TRANSDUCER PROTECTION

BACKGROUND OF THE INVENTION

The present invention relates generally to the protection of ultrasonic transducers from damage or distruction due to high temperature or the absence of a proper surrounding medium. More particularly, the invention relates to the protection of ultrasonic transducers used in ultrasonic nebulizers.

Ultrasonic nebulizers are utilized in the treatment of a variety of respiratory ailments and conditions. They may be used to humidify the atmosphere of a room, either with water vapor or some prescribed medicament, or they may be used in conjunction with respirator apparatus to provide the same functions. In the operation of a nebulizer, air or some other breathable mixture of gases is pumped through a chamber in the nebulizer in which a fountain of fine droplets of water or other liquid is maintained. A fountain is formed by the action of an ultrasonic transducer, typically a piezoelectric crystal, immersed in the liquid. The liquid to be nebulized is usually placed in a separate vessel separated from, and coupled to, a water chamber by a thin membrane. The transducer is immersed in the water chamber, and the ultrasonic energy is transmitted through the membrane to form the fountain in the medicament vessel.

A recurrent problem with ultrasonic nebulizers of this general type has been damaging ultrasonic transducers by reason of high temperatures, an absence of water surrounding the transducers, or both. Transducer protection has usually taken the form of a temperature detection device coupled to switch off the transducer in the event that some predetermined temperature is reached. Quite often, however, permanent damage can be done to a transducer soon after the surrounding water is gone from the transducer chamber, but before the temperature reaches the predetermined value. Accordingly, there is a definite need for a system of ultrasonic transducer protection which takes into account factors other than the temperature. The present invention fulfills this need.

SUMMARY OF THE INVENTION

The present invention resides in electrical means, and a corresponding method, for protecting an ultrasonic transducer which is normally immersed during operation in a surrounding fluid. Basically, and in general terms, the apparatus of the invention includes a first electrical means coupled with the transducer, for detecting surface motion of the surrounding fluid, and a second electrical means, coupled with the first, for switching the transducer off, when surface motion cannot be detected. The apparatus may additionally include means for detecting the temperature of the transducer, and means for logically combining signals representative of surface motion and temperature, to derive a control signal to switch the transducer on or off.

More specifically, the means for logically combining the surface motion and temperature signals includes means for switching the transducer off if surface motion is not detected and the temperature rises above a first predetermined level, and means for switching the transducer off if the temperature should rise above a second predetermined level greater than the first. Also included are means for locking the transducer in the off condition after being switched off, even if surface motion is subsequently detected, or if the temperature subsequently falls below the second or first predetermined levels. Consequently, after the transducer has been switched off because of high temperature or loss of surface motion, power must be turned off and on again before the transducer can be re-energized. Also included in the apparatus of the invention are means responsive to the application of electrical power, for resetting the means for locking the transducer in the off condition, and visual indicator means for indicating that the transducer has been switched off because of a high temperature or failure to detect surface motion in the fluid.

In terms of a novel method for protecting ultrasonic transducers, the invention comprises the steps of detecting the surface motion of the liquid in which the transducer is immersed, by analysis of the electrical voltage across the transducer terminals, and switching the transducer off if surface motion is absent. The method may also include the steps of detecting the temperature of the transducer, and switching the oscillator off if the surface motion is absent and the temperature is above a first predetermined level, or if the temperature is above a second predetermined level higher than the first. The step of detecting surface motion is effected by rectifying an electrical signal obtained from the terminals of the transducer, and thereby obtaining a binary electrical signal indicative of the presence or absence of random variations in the voltage across the transducer terminals. These random voltage variations are due to the random surface motion of the liquid in which the transducer is immersed.

It will be apparent from the foregoing that the present invention represents a significant advance in the protection of ultrasonic transducers, particularly as these devices are employed in ultrasonic nebulizers. The invention provides a reliable system for de-energizing transducers in the event of overheating, or in the absence of a liquid surrounding the transducer. Thus, transducer damage due to either of these conditions is consistently avoided, and transducer life is thereby greatly increased. Other aspects and advantages of the invention will become apparent from the more detailed description which follows, taken in conjunction with the accompanying drawings.

DESCRIPTION OF THE PREFERRED EMBODIMENT

Figure 1:
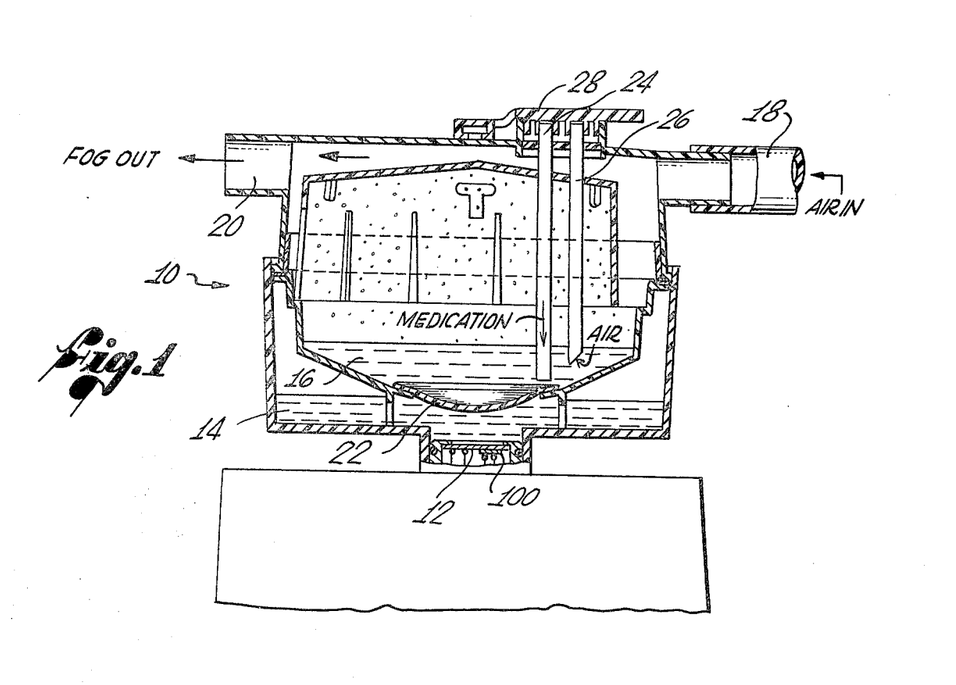
FIG. 1 is a simplified sectional view of an ultrasonic nebulizer of the general type with which the present invention may be used.

As shown in the drawings for purposes of illustration, the present invention is principally concerned with the protection of ultrasonic transducers, such as are used in ultrasonic nebulizers, from damage or destruction due to overheating or to the absence of a proper surrounding liquid. As shown in FIG. 1, which is a simplied view of an ultrasonic nebulizer (reference numberal 10), there is a transducer 12, usually of the piezoelectric type, which is located immersed in a water chamber 14. Located above the water chamber 14 is a medication chamber 16, which may be used to hold more water, or some liquid medicament which is to be nebulized into a fine mist.

Air, or an oxygen-enriched mixture, is drawn through an inlet tube 18 by a pump (not shown), passes through the medication chamber 16, and exits through an exit tube 20. The medication chamber 16 is separated from the water chamber 12 only by thin membrane or diaphragm 22, so that ultrasonic energy from the transducer 12 passes readily therethrough, and the transducer "sees" essentially only one body of liquid. The ultrasonic energy from the transducer raises in the liquid in the medication chamber 16 a fountain of very fine droplets, which are removed by the gas passing through the nebulizer, and are ultimately utilized to humidify or otherwise medicate a patient's breathable atmosphere.

Typically, nebulizers of this type also include a vertical medication feed tube 24 and a parallel vent tube 26, which may be used to maintain the medication liquid at a constant level in the chamber 16. A removable cap 28 is provided to seal off the tubes 24 and 26 when they are not being used.

One of the most common causes of breakdown of nebulizers of this type is damage to, or destruction of, the transducer due to overheating or to exhaustion of the liquid surrounding the transducer. Protection circuits depending only on temperature measurement or only on liquid level measurement have not proved totally effective in preventing such damage.

In accordance with the present invention, the presence of liquid is determined by the electrical detection of its surface motion, and signals indicative of both the surface motion of the liquid and the temperature of the transducer are utilized to derive an on/off signal for the transducer. Although digital logic elements are not employed in the presently preferred embodiment of the invention, the principles of operation of the invention can nevertheless be better explained and understood by reference to a simplified digital logic diagram, such as the one shown in FIG. 2. Accordingly, the invention will first be described with reference to FIG. 2, then the details of implementation of that logic will be explained with reference to the schematic diagram of FIG. 3.

Figure 2:
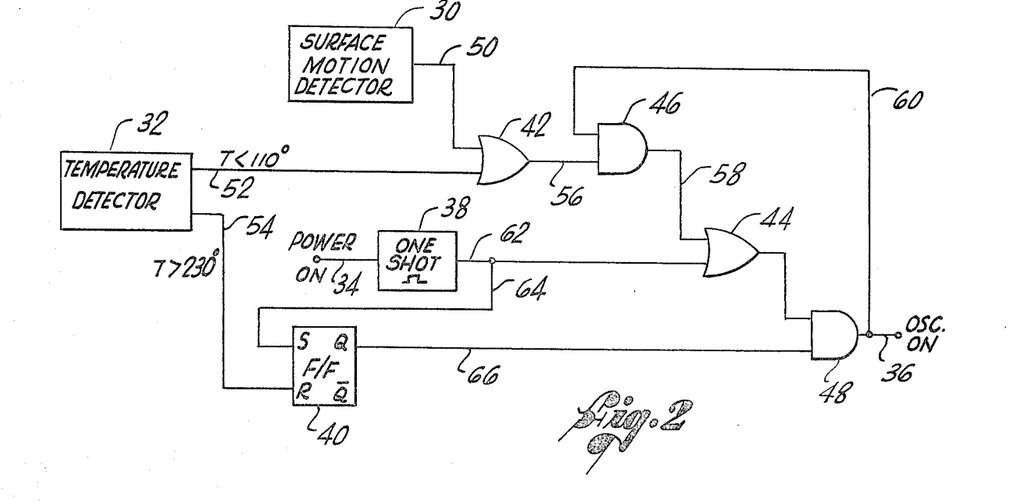
FIG. 2 is a simplified logic diagram illustrating the principals of operation of the present invention.

As shown in FIG. 2, the electrical apparatus of the invention utilizes inputs from a surface motion detector 30, a temperature detector 32, and a digital indication, as shown at 34, that power has been applied to the system. From these input signals, the apparatus generates as an output a transducer oscillator on/off signal, as shown at 36. The simplified logic diagram of FIG. 2 also includes a one-shot 38, a flip-flop 40, two OR gates 42 and 44, and two AND gates 46 and 48.

In operation, the surface motion detector 30 generates a logical one when surface motion is present, and a logical zero when surface motion is absent, on line 50, which is connected as an input to OR gate 42. The temperature detector 32 develops two outputs, one on line 52 indicative of whether the temperature is less than 110° F, and one on line 54 indicative of whether the temperature is greater than 230° F. The logic level on line 52 is one if the temperature is less than 110° F and is zero if the temperature is equal to or greater than 110° F. Similarly the logic level on line 54 is one if the temperature is greater than 230° F, and is zero if the logic level is less than 230° F.

Line 52 from the temperature detector is connected as another input to OR gate 42, the output of which is connected, by line 56, as an input to AND gate 46. The output of AND gate 46 is connected, in turn, as an input to the other OR gate 44, the output of which is connected, by line 58, as an input to the other AND gate 48. The latter AND gate output is the transducer oscillator on/off signal on line 36, and this is also connected, by line 60, as an input to the first AND gate 46. The signal from the temperature detector on line 54, indicative of whether the temperature is over 230° F, is connected to the reset terminal of the flip-flop 40. The power-on signal on line 34 is connected to energize the one-shot 38, which produces an output pulse approximately 500 milliseconds in duration on line 62 to the second OR gate 44. The output of the one-shot 38 is also connected, over line 64, to the set terminal of the flip-flop 40, the Q output of which is connected by line 66 to the other input of the second AND gate 48.

Inspection of the logic in FIG. 2 will show that, when electrical power is first applied to the system, the flip-flop 40 is set by the output from the one-shot 38 on line 64, i.e., its Q output is set to a logical one, and the output pulse from the one-shot also passes through the second OR gate 44, to the second AND gate 48. Since the output of the flip-flop 40 is one, the AND gate 48 has both of its inputs set to logical ones, and the oscillator on signal on line 36 is therefore a logical one, indicating that the oscillator will be turned on. It can further be seen from FIG. 2 that, if the temperature is less than 110° F, or if surface motion is detected, the first OR gate 42 will have a one output, and, for the period that the one-shot 38 is holding the oscillator on, the first AND gate 46 will be enabled by a one on line 60. Thus, a logical one will be applied to the second OR gate 44 over line 58, thereby maintaining the oscillator on signal. Consequently, so long as there is surface motion, or if the temperature is below 110° F, the transducer oscillator will be held in the on condition after the output pulse from the one-shot 38 has terminated.

Once the tranducer oscillator has been turned on as described above, it will also be apparent from FIG. 2 that the oscillator will be turned off again on the occurrence of either of two sets of conditions. First, if surface motion should cease, and if the temperature should go above 110° F, the first OR gate 42 will have a zero output, and this will be propogated through AND gate 46, OR gate 44 and AND gate 48, resulting in switching off of the oscillator. Second, if the temperature should rise above 230° F, whether or not surface motion is detected, the flip-flop 40 will be reset by the signal on line 54, resulting in a zero input to the second AND gate 48, and a zero output from the AND gate 48 to switch off the oscillator. Once the oscillator has been switched off by either of these conditions, the first AND gate 46 will be disabled because of the zero input on line 60. Thus, even if the surface motion should somehow be restored, and the temperature should drop below 110° F again, the AND gate 46 will still block re-energization of the oscillator. The on condition of the oscillator can then only be restored by removing and reapplying electrical power to the circuit, and thereby generating another output from the one-shot 38 and setting the flip-flop 40, as described above.

As already mentioned, the simplified digital logic diagram of FIG. 2 is intended primarily for purposes of explanation, and, for practical and economic reasons, there are no such purely digital logic elements in the presently preferred embodiment of the invention now to be described in connection with FIG. 3.

The surface motion detector 50 receives as input the ultrasonic transducer voltage, over lines 70 and 72. The surface motion of the water produces random variations in the electrical impedance of the transducer 12 (FIG. 1), since most of the ultrasonic energy incident upon the water-air interface is reflected and the nature of these reflections determines the acoustic impedance as seen by the vibrating transducer. When the surface is set into motion, such as by the spraying of droplets from the fountain generated in the medication chamber 16 (FIG. 1), the acoustic impedance seen by the transducer 12 changes in a random fashion determined by the exact nature of the surface motion at each instant in time. This variation in acoustic impedance produces corresponding changes in th electrical impedance, which manifest themselves as voltage amplitude variations at the transducer terminals. Therefore, the voltage at the transducer terminals, and across lines 70 and 72 is a radio-frequency signal whose amplitude varies in random fashion if surface motion is present in the water surrounding the transducer. As mentioned earlier, the water chamber 14 may be separated from the medication chamber 16 by the thin diaphragm 22, in which case the surface motion detected will be of the liquid in the medication chamber. When the liquid in the medication chamber 16 is exhausted, and there is still a full supply of water in the water chamber 14, no surface motion will be detected. The random amplitude variations in the transducer voltage will, of course, have a frequency much less than the radio-frequency signal applied to the transducer.

Basically, the surface motion detector 50 includes a rectifier circuit 74, a peak detector circuit 76, an amplifier circuit 78, and a threshold detection circuit 80. These circuits can be implemented in any of a variety of ways, and their design details are not considered to be critical to the invention. The function of the surface motion detector 50 is to make a threshold measurement of the random variations in transducer voltage amplitude. An output signal is generated on line 82 depending upon whether the measured variations are above or below a predetermined threshold. In the detailed circuitry of the surface motion detector 50 shown in FIG. 3 by way of example, the rectifier circuit 74 removes the radio-frequency component of the transducer voltage signal, leaving on line 84 from the rectifier circuit a signal principally comprised of a d.c. level equivalent to the average transducer voltage, together with random signal variations about the d.c. level if there is surface motion in the water. The d.c. level is blocked by a capacitor 86, leaving a signal which randomly varies about a zero reference point.

The peak detector circuit 76, which includes a capacitor 88 and a diode 90, produces at its output, shown at 92, a d.c. voltage signal equivalent to the peak value of the random voltage variations. A zener diode 94 clips this peak value to a maximum permissible value. The amplifier circuit 78 amplifies this peak value before it is applied over line 96 to the threshold detection circuit 80, for comparison with a fixed threshold level. The threshold detection circuit 80 includes a comparator 98, the negative terminal of which is supplied with the random voltage signal over line 96, and the positive terminal of which is supplied with a fixed threshold voltage. The output on line 82 from the comparator 98, which is also the output from the surface motion detector 50, is an open-collector output which is set to a low level only if a threshold degree of surface motion is detected, and is open-circuited if the surface motion threshold is not reached.

The temperature detector 32 (FIG. 2) includes a thermistor 100 which is soldered or otherwise bonded to the transducer 12 (FIG. 1) to provide an accurate indication of its temperature. As can be seen in FIG. 3, the thermistor 100 has one terminal connected to a common return, and the other terminal connected to the negative terminal of a comparator 102 and to the positive terminal of another comparator 104. A resistor 106 is connected between a power supply bus 108 and the negative terminal of comparator 102, so that resistor 106 and thermistor 100 form a voltage divider. The voltage applied to the negative terminal of comparator 102 and to the positive terminal of comparator 104 therefore depends upon the resistance value of the thermistor 100. The positive the resistance value of the thermistor 100. The positive terminal of comparator 102 is biased to a voltage value determined by another voltage divider, consisting of a resistor 110 connected from the power supply bus 108 to the positive terminal of comparator 102, and a resistor 112 from the positive terminal of comparator 102 to the common return. A feedback resistor 114 is connected between the output of the comparator 102 and its positive terminal.

When the transducer temperature is relatively low, the thermistor resistance is relatively high, and the negative terminal of comparator 102 is at a relatively high potential, resulting in a low level output on line 116. With the output on line 116 low, the feedback resistor 114 is essentially paralleled with the resistor 112 and the voltage on the positive terminal of comparator 102 is thereby maintained at a low level with respect to the negative terminal. The resistance values are chosen such that, when the temperature reaches 110° F, the voltage at the negative terminal of comparator 102 has fallen to a level below that on the positive terminal, and the output on line 116 then switches from a low level to a high or open-circuit level. This effectively removes the feedback resistor 114 from the biasing circuit of comparator 102, and thereby raises the bias on the positive terminal to such an extent that, when the temperature is lowered below 110° F, the voltage on the negative terminal of comparator 102 will not be high enough to switch the output to a low level again until the temperature is lowered to some very low value, such as 30° F.

Up to this point, it can be seen that a low level on line 82 indicates detected surface motion, and a low level on line 116 indicates a temperature of less than 110° F. These two lines 82 and 116 are electrically connected, as shown at the junction 118, and if either one or both of them is at a low voltage level, the junction 118 will be at a low voltage level. The junction 118 is connected through a resistor 120 to the positive terminal of another comparator 122, which is itself connected through a resistor 124 to the power supply bus 108. Thus, if the junction 118 is held at a low level, the resistors 124 and 120 form a voltage divider which applies a relatively low voltage level to the positive terminal of comparator 122. If the junction 118 is not held at a low level, the positive terminal of comparator 122 is held at a relatively high voltage level determined by the power supply voltage.

The negative terminal of comparator 122 is biased to a value substantially less than the power supply voltage by means of a voltage divider consisting of resistors 126 and 128 connected between the power supply bus 108 and a common return. The output of comparator 122, on line 36, is the transducer oscillator on/off signal, a low level indicating an on condition, and a high level indicating an off condition. It should be apparent from this description that, when the positive terminal of comparator 122 is forced to a low potential by virtue of the presence of surface motion in the water or a temperature below 110° F, the output signal on line 36 will be a low, or an on signal. However, if there is neither detected surface motion nor a temperature below 110° F, the positive terminal of comparator 122 will be at a potential above that of the negative terminal, and the output on line 36 will be high, indicating an off signal to the transducer oscillator.

The thermistor 100 is also connected to the positive terminal of comparator 104, the negative terminal of which is biased by means of a voltage divider consisting of resistors 130 and 132 connected between the power supply bus 108 and the common return. The values of these resistors 130 and 132 are selected such that when the transducer temperature is below 230° F, the voltage on the positive terminal of comparator 104 exceeds that on the negative terminal, and the output on line 134 is high or open-circuited. However, when the transducer temperature goes above 230° F, the voltage on the positive terminal of comparator 104 falls below the voltage of the negative terminal, and the output on line 134 is forced to a lower level. This has two immediate effects. First, comparator 104 is latched in this condition, because a feedback diode 136 with its anode connected to the positive terminal and its cathode connected to the output line 134, so that, when the voltage on the output line is forced to a low level, the diode is placed in a conductive state and essentially holds the output line at the low level until power is removed from the circuit. Second, the low level output on the output line 134, which is also connected to the negative terminal of comparator 122, lowers the voltage at that terminal, and forces the oscillator on/off signal on line 36 to a high or off condition. Thus, when the transducer temperature exceeds 230° F, the transducer oscillator is forced to an off condition, regardless of whether surface motion is still being detected.

From the detailed description thus far, correspondence with the logic diagram of FIG. 2 can be readily seen. The junction 118 is FIG. 3 functions as the OR gate 42 of FIG. 2, and the comparator 104 with its feedback diode 136 are logically equivalent to the flip-flop 40 (FIG. 2), which is reset when the temperature goes above 230° F, and is set only when power is applied to the circuit. The comparator 122 is logically equivalent to the AND gate 48 (FIG. 2), since, in order to produce an on condition at the output on line 36, the positive terminal must be low, as derived from the detection of surface motion or a temperature below 110° F, and the negative terminal must be allowed to remain relatively high, i.e., the temperature must be below 230° F.

Figure 3:
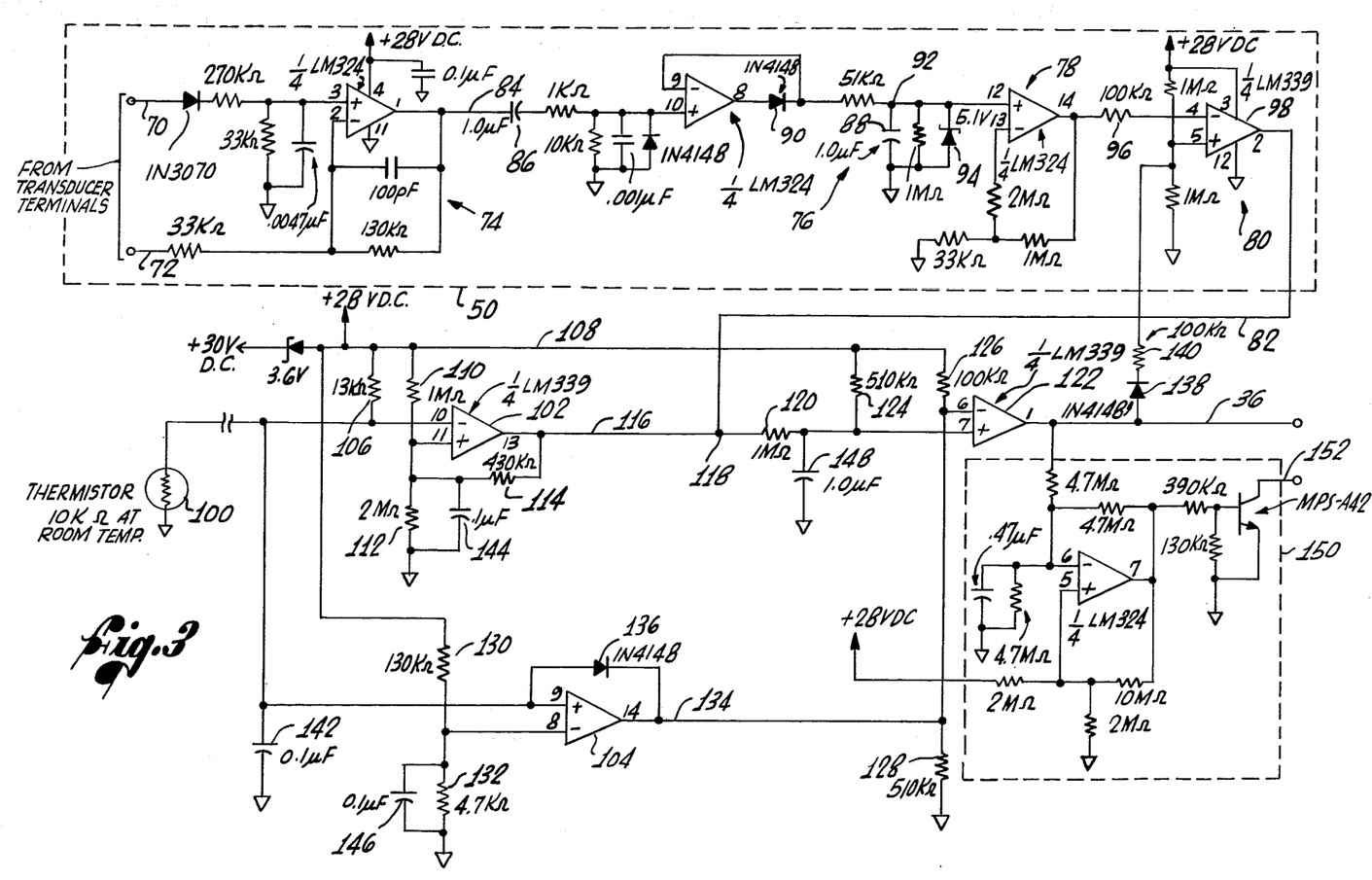
FIG. 3 is a detailed schematic diagram of the transducer protection circuit of the present invention.

The other AND gate 46 of FIG. 2 also has its equivalent in the detailed circuitry of FIG. 3. When the transducer oscillator is turned off as a result of loss of surface motion and a temperature of over 110° F, comparator 102 has a high level output on line 116, and, as has been mentioned, this level will be locked in a high condition even when the temperature falls back below 110° F. This hysteresis or latching characteristic of the comparator 102 circuit functions in a manner analogous to AND gate 46 to prevent a subsequent turning on of the oscillator when the temperature falls below 110° F.

It is physically unlikely that surface motion would be detected after the transducer oscillator had been turned off, but, to prevent re-energization of the oscillator after turning off, a feedback path is provided to disable the surface motion detector 50 once the oscillator has been turned off. The feedback path includes a diode 138 and a resistor 140 connected in series between the output line 36 of comparator 122 and the positive terminal of comparator 98 of the threshold detection circuit 80. When the oscillator is turned off as indicated by a high level on the output line 36, this high level is transmitted to the positive terminal of the comparator 98, thus insuring that a high level output results on line 82, indicating no surface motion of the water. It can be seen, therefore, that, after the oscillator has been switched to an off condition by any of the alternatives described, the latching effect of comparator 102, together with the feedback path through the diodes 138 and resistor 140 to the threshold detection circuit 80, function in the same way as the AND gate 46 of FIG. 2 to prevent re-energization of the oscillator after it has been turned off.

Still to be discussed is the sequence of events which occurs when power is first applied to the circuitry of FIG. 3. Because the comparator 102 will latch with its output in a high condition, and comparator 104 will latch with its output in a low condition, means must be included to insure that both of these comparators do not come up in their latched conditions when power is first applied. This is achieved by use of R-C circuits, with appropriately selected values, to control the rate of rise of certain voltages in these comparator circuits. A capacitor 142 is connected across the thermistor 100, so that the rate at which the voltage at the thermistor rises when power is applied is determined by the value of the capacitor 142 and the value of the resistor 106. Similarly a capacitor 144 is connected between the positive terminal of amplifier 102 and the common return, and a third capacitor 146 is connected between the negative terminal of comparator 104 and the common return. The values of these capacitors 142, 144 and 146 are chosen such that, in the case of comparator 102, the voltage on the positive terminal rises at a slower rate than the voltage on the negative terminal. Consequently, the output on line 116 will initially be low as power is applied. Similarly, in the case of the comparator 104, the voltage on the negative terminal when power is first applied rises at a slower rate than the voltage on the positive terminal, thus insuring that the output on line 134 is high. Consequently, when power is first applied comparators 102 and 104 initially have low and high outputs, respectively, so that they do not immediately latch.

The effect of the one-shot 38 of FIG. 2, is obtained in the detailed circuitry by means of a capacitor 148 connected between the positive terminal of comparator 122 and the common return. When power is applied to the system, this capacitor 148 begins charging through the resistor 124 which is connected to the power supply bus 108. The value of the capacitor 148 is selected such that the voltage on the positive terminal of comparator 122 will be lower than that on the negative terminal for a period of approximately 500 milliseconds, thus insuring that the output on line 36 will be low for this period, and that the oscillator will therefore be held on for at least this period of time. This enforced on period of the oscillator immediately upon the application of power will occur regardless of the potential at junction 118, so that the capacitor circuit is functioning in essentially the same way as the one-shot 38 supplying a signal through the OR gate 44 of FIG. 2. In a normal situation, before the 500-millisecond period is complete, surface motion will be detected and the temperature will probably be below 110° F, so that the voltage at the junction 118 will be at a low level, and the oscillator will consequently remain in an on condition even after the 500-millisecond period has ended.

The only circuitry of FIG. 3 remaining to be discussed is a warning oscillator circuit 150 which is connected to the output line 36 of comparator 122. When the output line 36 goes high, indicating that the transducer oscillator has been turned off for some danger condition, the warning oscillator circuit 150 generates a cyclic on/off signal at its output on line 152, which may be connected to drive a neon lamp, not shown, or other warning device.

It will be apparent that any of a wide variety of components may be used in the circuitry of FIG. 3. By way of example only, the component values and standard part numbers shown in FIG. 3 are those presently used in the preferred embodiment of the invention.

It can be seen from the foregoing that the present invention represents a significant advance in the field of ultrasonic transducer protection. In particular, the invention utilizes the detection of both surface motion of the water surrounding the transducer, and the temperature of the transducer, to derive a transducer control signal. In addition, once the transducer oscillator has been switched off because of loss of surface motion or high temperature, the oscillator cannot be re-energized unless power is removed and again applied to the system. It will also be appreciated that, although a particular embodiment of the invention has been described in detail for purposes of illustration, various refinements and modifications can be made without departing from the spirit of the invention. Accordingly, the scope of the invention is not to be limited, except as by the appended claims.

I Claim:

1. Apparatus for the protection of an ultrasonic transducer designed to operate while immersed in a liquid, said apparatus comprising:
   first electrical means coupled with the transducer, for detecting surface motion of the liquid; and
   second electrical means coupled with said first electrical means, for switching the transducer off when surface motion of the liquid cannot be detected, whereby the non-existence of surface motion in the liquid when the transducer is in an on condition indicates that liquid is not present and that the transducer is therefore subject to damage or destruction.

2. Apparatus as set forth in claim 1, wherein:
   said first electrical means monitors a radio-frequency signal applied to energize the transducer; and
   said first electrical means includes rectifying and filtering means for removing radio-frequency components of the monitored signal, peak detection means for detecting a peak value of random amplitude variations in the monitored signal, and comparator means for comparing the detected peak value with a fixed threshold level;
   whereby significant surface motion of the liquid causes random variations in the pattern of ultrasonic energy reflected back from the surface, which in turn causes random variations in the acoustic impedance and the electrical impedance of the transducer, thereby generating random amplitude variations in the electrical voltage between the transducer terminals.

3. Apparatus as set forth in claim 1, and further including means for locking the transducer in an off condition after switching off by said second electrical means, whereby the transducer can be switched on again only by removal and reapplication of electrical power to said apparatus.

4. Apparatus as set forth in claim 1, and further including means for overriding said first electrical means and switching the transducer on for at least a brief period of time when electrical power is first applied to said apparatus, whereby, if liquid is present, surface motion will be detected during said brief period of time, and said first electrical means will hold the transducer in an on condition after said brief period of time has elapsed.

5. Apparatus for the automatic protection of an ultrasonic transducer which is operated immersed in a liquid, said apparatus comprising:
   surface motion detection means coupled to the transducer and operable to generate an electrical signal when the surface motion of the liquid exceeds a predetermined threshold level;
   transducer temperature detection means, including means for generating a first temperature signal if the transducer temperature exceeds a first predetermined value, and means for generating a second temperature signal if the transducer temperature exceeds a second predetermined value greater than the first predetermined value; and
   electrical means coupled with said surface motion detection means and said temperature detection means, for switching the transducer to an off condition if the transducer temperature exceeds the first predetermined value and no surface motion is detected, or if the transducer temperature exceeds the second predetermined value;
   whereby the transducer is permitted to remain in an on condition if its temperature is below the first predetermined value, even if there is no surface motion, in order to permit adjustment of the transducer without its being automatically turned off when surface motion stops.

6. Apparatus as set forth in claim 5, and further including means for locking the transducer in the off condition after switching off by said electrical means, whereby the transducer will remain switched off even if surface motion should be subsequently detected or if the transducer temperature should subsequently fall below the second or first predetermined values.

7. Apparatus as set forth in claim 5, and further including means for overriding said electrical means and switching the transducer on for at least a brief period of time when electrical power is initially applied to said apparatus, whereby the transducer may be switched on when surface motion is initially absent and the transducer temperature is above the first predetermined level, and whereby the transducer will remain in the on condition after the brief period of time provided surface motion is detected during that time and the transducer temperature does not exceed the second predetermined level.

8. Apparatus as set forth in claim 5, and further including alarm indication means coupled with said electrical means, for indicating that the transducer has been switched off because of lack of surface motion or because of high temperature.

9. Apparatus as set forth in claim 5, wherein said surface motion detection means includes:
rectifying and filtering means coupled to the transducer for removing radio-frequency components in the electrical voltage as monitored at the transducer terminals;
peak detection means for detecting peak values of random amplitude variations in the voltage signal across the transducer terminals; and
comparator means for comparing the detected peak values of random amplitude variations with a fixed threshold value, and thereby generating a signal indicative of the presence or absence of surface motion in the liquid.

10. Apparatus for the automatic protection of an ultrasonic transducer which is operated immersed in a liquid, said apparatus comprising:
surface motion detection means coupled to the transducer and operable to generate an electrical signal when the surface motion of the liquid exceeds a predetermined threshold level;
transducer temperature detection means, including means for generating a first temperature signal if the transducer temperature exceeds a first predetermined value, and means for generating a second temperature signal if the transducer temperature exceeds a second predetermined value greater than the first predetermined value;
electrical means coupled with said surface motion detection means and said temperature detection means, for switchng the transducer to an off condition if the transducer temperature exceeds the first predetermined value and no surface motion is detected, or if the transducer temperature exceeds the second predetermined value, whereby the transducer is permitted to remain in an on condition if its temperature is below the first predetermined value, even if there is no surface motion, in order to permit adjustment of the transducer without its being automatically turned off when surface motion stops;
means for locking the transducer in the off condition after switching off by said electrical means, whereby the transducer will remain switched off even if surface motion should be subsequently detected or if the transducer temperature should subsequently fall below the second or first predetermined values;
means for overriding said electrical means and switching the transducer on for at least a brief period of time when electrical power is initially applied to said apparatus, whereby the transducer may be switched on when surface motion is initially absent and the transducer temperature is above the first predetermined level, and whereby the transducer will remain in the on condition after the brief period of time provided surface motion is detected during that time and the transducer temperature does not exceed the second predetermined level; and
alarm indication means coupled with said electrical means, for indicating that the transducer has been switched off because of lack of surface motion or because of high temperature.

11. A method for automatically protecting an ultrasonic transducer which normally operates immersed in a liquid, said method comprising the steps of:
detecting surface motion in the liquid by analysis of the electrical voltage across the terminals of the transducer; and
switching off the transducer if said detecting step indicates no surface motion of the liquid, whereby absence of surface motion is indicative of absence of liquid or maladjustment of the transducer.

12. A method as set forth in claim 11 wherein said detecting step includes:
rectifying and filtering the voltage across the transducer terminals to remove radio-frequency components;
detecting peak values of random variations in the signal remaining after rectifying and filtering if surface motion is present; and
comparing the detected peak values with a fixed threshold value to determine whether or not there is surface motion on the liquid.

13. A method as set forth in claim 11, and further including the step of locking the transducer in an off condition after turning off by said switching step, thereby preventing re-energization of the transducer until electrical power has been removed and reapplied.

14. A method as set forth in claim 11, and further including the step of initially overriding said step of switching the transducer off, and switching the transducer on during the initial application of electrical power for a short period of time, whereby the transducer may be initially energized although surface motion will be absent, and will remain energized if surface motion is detected during the brief period of time.

15. A method for the protection of an ultrasonic transducer which normally operates immersed in a liquid, said method comprising the steps of:
detecting the surface motion of the liquid by analysis of the electrical voltage signal between the terminals of the transducer;
detecting the temperature of the transducer;
generating a first temperature signal if the transducer temperature exceeds a first predetermined value;
generating a second temperature signal if the temperature of the transducer exceeds a second predetermined value greater than the first; and
switching off the transducer when no surface motion is detected and the transducer temperature exceeds the first predetermined value, or when the transducer temperature exceeds the second predetermined value.

16. A method as set forth in claim 15, and further including the step of locking the transducer in an off condition after switching off by said switching step, whereby the transducer will remain in the off condition even if surface motion is resumed and the transducer temperature falls below the second or first predetermined values.

17. A method as set forth in claim 15, and further including the step of switching the transducer on initially at least for a brief period of time, said step of switching on overriding said step of switching for the brief period of time, whereby the transducer will remain in the on condition if the transducer temperature falls below the second predetermined value, and if surface motion begins or the transducer temperature falls below the first predetermined value, all during the brief time period.

18. A method as set forth in claim 15, and further including a step of actuating an alarm signal whenever said step of switching off the transducer takes place, whereby the condition which caused switching off of the transducer may be brought to the attention of an operator and corrected,.

19. A method as set forth in claim 15, wherein said step of detecting surface motion of the liquid includes:

rectifying and filtering the voltage signal across the transducer to remove radio-frequency components thereof;

detecting peak values in the remaining signal due to random variations in signal amplitude caused by surface motion; and comparing the detected peak values with a fixed threshold value to determine whether or not surface motion exists.

* * * * *

UNITED STATES PATENT AND TRADEMARK OFFICE
CERTIFICATE OF CORRECTION

PATENT NO. : 4,001,650
DATED : September 2, 1975
INVENTOR(S) : Jack Romain

It is certified that error appears in the above-identified patent and that said Letters Patent are hereby corrected as shown below:

Column 5, line 15, "th" should be --the--.

Column 7, line 47, "is" should be --in--.

Signed and Sealed this

Twenty-eighth Day of June 1977

[SEAL]

Attest:

RUTH C. MASON
Attesting Officer

C. MARSHALL DANN
Commissioner of Patents and Trademarks